(12) United States Patent
Liberatore et al.

(10) Patent No.: US 8,188,133 B2
(45) Date of Patent: May 29, 2012

(54) IMIDAZOLE DERIVATIVES, PREPARATION AND USER THEREOF AS MEDICINE

(75) Inventors: Anne-Marie Liberatore, Auffargis (FR); Dennis Bigg, Gif sur Yvette (FR); Dominique Pons, Paris (FR); Grégoire Prevost, Antony (FR)

(73) Assignee: Ipsen Pharma S.A.S., Paris (FR)

( * ) Notice: Subject to any disclaimer, the term of this patent is extended or adjusted under 35 U.S.C. 154(b) by 74 days.

(21) Appl. No.: 12/298,757

(22) PCT Filed: Apr. 26, 2007

(86) PCT No.: PCT/FR2007/000706
§ 371 (c)(1),
(2), (4) Date: Mar. 11, 2009

(87) PCT Pub. No.: WO2007/125197
PCT Pub. Date: Nov. 8, 2007

(65) Prior Publication Data
US 2009/0186930 A1      Jul. 23, 2009

(30) Foreign Application Priority Data
Apr. 27, 2006   (FR) .................................... 06 03783

(51) Int. Cl.
*A61K 31/33* (2006.01)
*C07D 233/58* (2006.01)

(52) U.S. Cl. ...................................... 514/396; 548/343.5
(58) Field of Classification Search ................... 514/396; 548/343.5; 552/343.5
See application file for complete search history.

(56) References Cited

U.S. PATENT DOCUMENTS
7,534,805 B2 * 5/2009 Bigg et al. .................... 514/396

FOREIGN PATENT DOCUMENTS
WO   WO 03/075921 A2   9/2003

OTHER PUBLICATIONS

Voskoglou-Nomikos et al., Clinical Cancer Research, vol. 9, pp. 4227-4239, Sep. 12, 2003.*
Form PCT/ISA/210 in International Patent Application No. PCT/FR2007/000706.
Gould, "Salt selection for basic drugs," *International Journal of Pharmaceutics*, 33: 201-17 (1986).

* cited by examiner

*Primary Examiner* — Sabiha Qazi
(74) *Attorney, Agent, or Firm* — Hunton & Williams LLP

(57) ABSTRACT

The invention concerns novel imidazole derivatives of general formula (I), wherein Z' and Z represent different variable groups. Said products have an antitumoral activity. The invention also concerns pharmaceutical compositions containing said products and their use for preparing antitumoral medicine.

9 Claims, No Drawings

IMIDAZOLE DERIVATIVES, PREPARATION AND USER THEREOF AS MEDICINE

CROSS-REFERENCE TO RELATED APPLICATIONS

This application is the U.S. National Phase Application of International Application No. PCT/FR2007/000706, filed Apr. 26, 2007, which claims the benefit of French Application No. FR 06/03783, filed Apr. 27, 2006, the disclosures of each of which are hereby incorporate by reference.

FIELD OF INVENTION

A subject of the present Application is novel imidazole derivatives. The invention also relates to pharmaceutical compositions containing these derivatives and their use for the preparation of a medicament.

The imidazole derivatives according to the present invention have an anti-tumoral activity and in particular an inhibitory activity on tubulin polymerization.

BACKGROUND

The target of several antineoplastic medicaments, tubulin is a small-sized protein which, on polymerizing, produces the microtubules of the mitotic spindle which allows cell division during mitosis. The vinca-alkaloids inhibit its polymerization, whereas paclitaxel and docetaxel excessively stabilize it. In both cases, mitosis cannot take place normally, which hinders cell proliferation.

SUMMARY OF INVENTION

Due to their anti-tumoral activity, the compounds according to the invention can be used for the treatment of tumors or cancers comprising cancers of the oesophagus, the stomach, the intestines, the rectum, the oral cavity, the pharynx, the larynx, the lung, the colon, the breast, the cervix uteri, the corpus endometrium, the ovaries, the prostate, the testes, the bladder, the kidneys, the liver, the pancreas, the bones, the connective tissues, the skin, the eyes, the brain and the central nervous system, as well as cancer of the thyroid gland, leukaemia, Hodgkin's disease, non-Hodgkin's lymphomas, multiple myelomas and others. Moreover, these compounds can also be used to treat certain viral infections such as acquired immunodeficiency syndrome, hepatitis C as well as auto-immune diseases and certain degenerative diseases.

The compounds according to the invention can also be used for treating diseases such as gout, rheumatic diseases such as for example familial Mediterranean fever and all other inflammatory diseases (Ben-Chetrit E.; Bergmann S.; Sood R.; *Rheumatology* 2005; 1-9).

A subject of the present invention is therefore a compound of general formula (I)

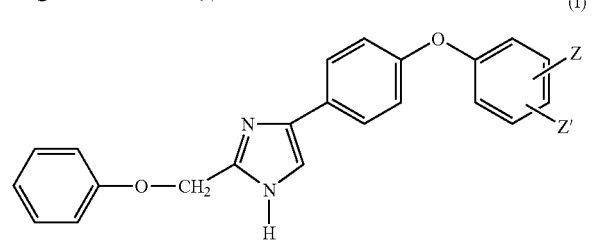

(I)

in racemic, enantiomeric form or any combination of these forms, in which:

Z' represents the hydrogen atom or the halo radical;
Z represents a radical of formula —NH—X—NR$_1$R$_2$;
R$_1$ and R$_2$ represent, independently, the hydrogen atom, a (C$_1$-C$_6$)alkyl radical, phenyl optionally substituted by a (C$_1$-C$_6$)alkyl radical, or benzyl optionally substituted on the ring by a (C$_1$-C$_6$)alkyl radical;
X represents —SO$_2$— or

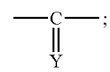

Y represents S, O, CH—R or N—R;
R represents —CN or —NO$_2$;
or a pharmaceutically acceptable salt thereof, The invention covers all the tautomeric forms of the compounds of formula (i) as defined above.

In the definitions indicated above, the expression halo (halogeno) represents the fluoro, chloro, bromo or iodo, preferably fluoro, chloro or bromo radical. The expression (C$_1$-C$_6$) alkyl represents an alkyl radical having 1 to 6 carbon atoms, linear or branched, such as the methyl, ethyl, propyl, isopropyl, butyl, isobutyl, sec-butyl and tert-butyl, pentyl or amyl, isopentyl, neopentyl, 2,2-dimethyl-propyl, hexyl, isohexyl or 1,2,2-trimethyl-propyl radicals.

Preferably, the invention relates to a compound of formula (I) as defined above and characterized in that R$_1$ and R$_2$ represent, independently, the hydrogen atom or a (C$_1$-C$_6$) alkyl radical. Very preferably, R$_1$ represents the hydrogen atom and R$_2$ the hydrogen atom or a (C$_1$-C$_6$)alkyl radical.

Preferably also, the invention relates to a compound of formula (I) as defined above and characterized in that X represents —C(Y)— and Y represents S, O, CH—R or N—R. Very preferably, the invention relates to a compound of formula (I) as defined above and characterized in that X represents —C(Y)— and Y represents S, O or N—R. Very preferably also, the invention relates to a compound of formula (I) as defined above and characterized in that X represents —C(Y)— and Y represents S or N—R and R represents —CN.

Preferably also, the invention relates to a compound of formula (I) as defined above and characterized in that X represents —SO$_2$.

Preferably, the invention relates to a compound of formula (I) as defined above and characterized in that Z is in para position.

Preferably, the invention relates to a compound of formula (I) as defined above and characterized in that Z' is in meta position.

Preferably, the invention relates to a compound of formula (I) as defined above and characterized in that Z' represents the halo radical and preferably fluoro.

A subject of the invention is also the compounds as illustrated in the experimental part and characterized in that they correspond to one of the following formulae:

N-(4-methylphenyl)-N'-(4-{4-[2-(phenoxymethyl)-1H-imidazol-4-yl]phenoxy}phenyl)urea;

N-butyl-N'-(4-{4-[2-(phenoxymethyl)-1H-imidazol-4-yl]
    phenoxy}phenyl)urea trifluoroacetate;

N-(4-{4-[2-(phenoxymethyl)-1H-imidazol-4-yl]
    phenoxy}phenyl)urea;

N-ethyl-N'-(4-{4-[2-(phenoxymethyl)-1H-imidazol-4-yl]
    phenoxy}phenyl)thiourea;

N-ethyl-N'-(2-fluoro-4-{4-[2-(phenoxymethyl)-1H-imida-
    zol-4-yl]phenoxy}phenyl)thiourea;

N-(2-fluoro-4-{4-[2-(phenoxymethyl)-1H-imidazol-4-yl]
    phenoxy}phenyl)thiourea;

N-isopropyl-N'-(4-{4-[2-(phenoxymethyl)-1H-imidazol-4-
    yl]phenoxy}phenyl)urea;

N-(4-{4-[2-(phenoxymethyl)-1H-imidazol-4-yl]
    phenoxy}phenyl)-N'-phenylurea;

N-(4-methylbenzyl)-N'-(4-{4-[2-(phenoxymethyl)-1H-imi-
    dazol-4-yl]phenoxy}phenyl)urea;

N-ethyl N' (4-{4-[2-(phenoxymethyl)-1H-imidazol-4-yl]
    phenoxy}phenyl)urea trifluoroacetate;

N-(2-fluoro-4-{4-[2-(phenoxymethyl)-1H-imidazol-4-yl]
    phenoxy}phenyl)sulfamide hydrochloride;

N"-cyano-N-(2-fluoro-4-{4-[2-(phenoxymethyl)-1H-imida-
    zol-4-yl]phenoxy}phenyl)guanidine;

N-(2-fluoro-4-{4-[2-(phenoxymethyl)-1H-imidazol-4-yl]
    phenoxy}phenyl)-N"-nitroguanidine;

and more particularly to one of the following formulae:

N-(4-{4-[2-(phenoxymethyl)-1H-imidazol-4-yl]
    phenoxy}phenyl)urea;

N-ethyl-N-(4-{4-[2-(phenoxymethyl)-1H-imidazol-4-yl]
    phenoxy}phenyl)thiourea;

N-ethyl-N'-(2-fluoro-4-{4-[2-(phenoxymethyl)-1H-imida-
    zol-4-yl]phenoxy}phenyl)thiourea;

N-(2-fluoro-4-{4-[2-(phenoxymethyl)-1H-imidazol-4-yl]
    phenoxy}phenyl)thiourea;

N-(2-fluoro-4-{4-[2-(phenoxymethyl)-1H-imidazol-4-yl]
    phenoxy}phenyl)sulfamide hydrochloride;

N"-cyano-N-(2-fluoro-4-{4-[2-(phenoxymethyl)-1H-imida-
    zol-4-yl]phenoxy}phenyl) guanidine;

N-(2-fluoro-4-{4-[2-(phenoxymethyl)-1H-imidazol-4-yl]
    phenoxy}phenyl)-N"-nitroguanidine.

DETAILED DESCRIPTION OF THE PREFERRED EMBODIMENTS

Depending on the definitions of the Z and Z' variable groups, the compounds according to the invention can be prepared according to the procedures A to E described below.

As described in Diagram A below, the compounds of general formula (I) in which $R_2$ represents the hydrogen atom and $R_1$ represents the hydrogen atom, a ($C_1$-$C_6$)alkyl radical, optionally substituted phenyl radical or optionally substituted benzyl radical, X represents the —C(Y)— radical and Y an oxygen or sulfur atom, can be obtained from commercial isocyanate or isothiocyanate compounds of general formula (II) according to standard organic synthesis methods known to a person skilled in the art.

Diagram A

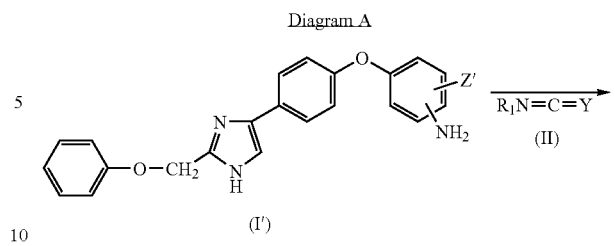

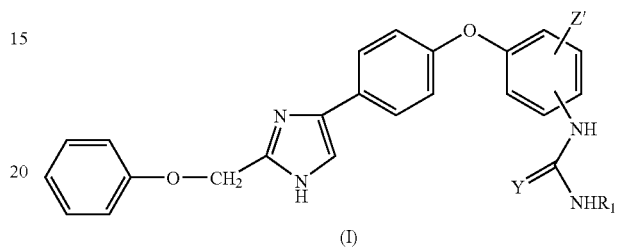

The aniline derivatives of general formula (I') can be prepared according to the method described in WO 2004/106307.

As described in Diagram B below, the compounds of general formula (I) in which $R_1$ and $R_2$ are hydrogen atoms, X represents the —C(Y)— radical and Y an oxygen or sulfur atom, can be, for example, obtained by reacting (thio)phosgene of formula $Cl_2C=Y$ in an inert solvent such as tetrahydrofuran or dioxane, with the aniline derivative (I') in order to form the iso(thio)cyanate derivative of general formula (III) followed by a condensation of gaseous ammonia in a solvent such as tetrahydrofuran or dichloromethane in order to form the compound of general formula (I).

Diagram B

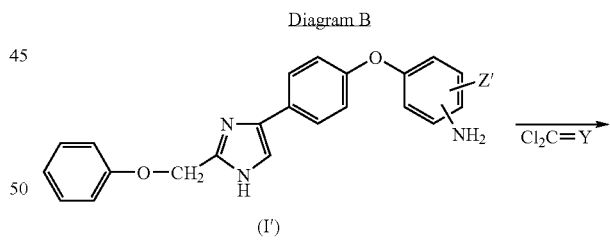

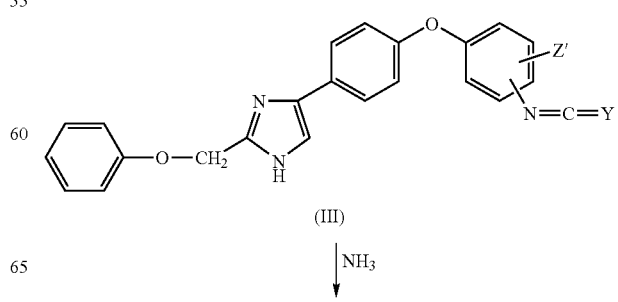

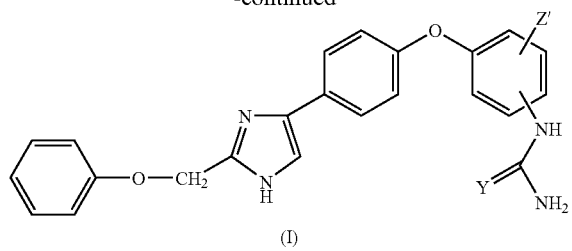
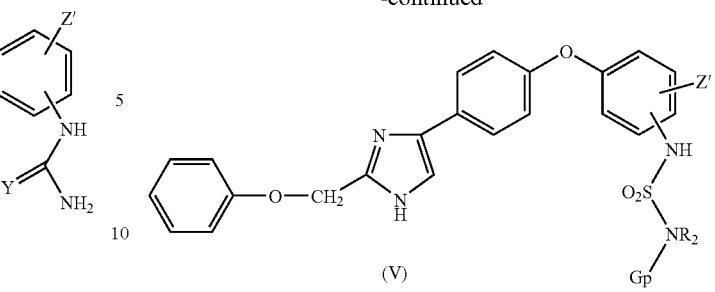

As described in Diagram C below, the compounds of general formula (I) in which $R_1$ represents the hydrogen atom and $R_2$ the hydrogen atom or an alkyl radical, and X represents an —$SO_2$— radical, can be easily obtained by deprotection of the intermediates of general formula (V) in which Gp is a protective group of an amine function (for example a protective group of carbamate type or any other protective group known to a person skilled in the art and in particular those mentioned in: *Protective groups in organic synthesis,* 2nd ed., (John Wiley & Sons Inc., 1991)). The derivatives of general formula (V) can be obtained by reacting the sulfonyl halide compounds protected by a protective group Gp as defined above of general formula (IV) which are prepared according to the method described in *Biorganic & Medicinal Chemistry Letters,* 13 (2003), 837-840, with the aniline derivative of general formula (I').

Diagram C

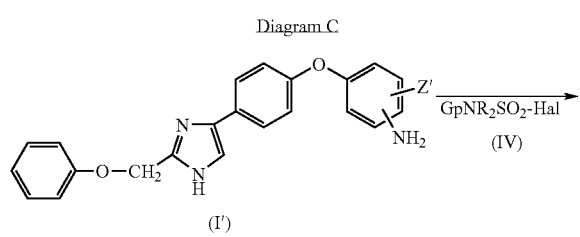

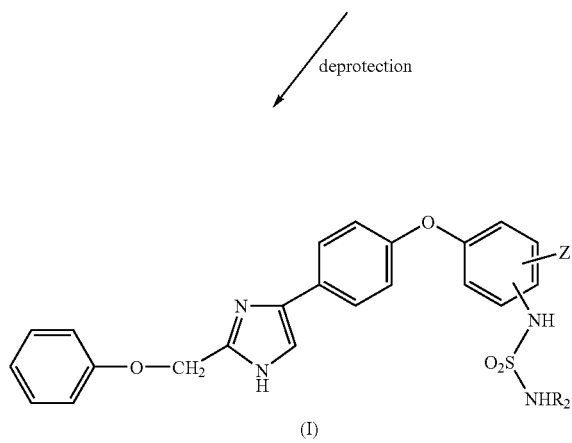

As described in Diagram D below, the compounds of general formula (I) in which $R_1$ and $R_2$ are hydrogen atoms, X represents the —C(Y)— radical and Y the N—$NO_2$ radical, can be easily obtained by heating under reflux a solvent such as acetonitrile, the nitrated derivative of general formula (VI) in which G'p is a leaving group such as the dimethylpyrazole or pyrazole groups, with the aniline derivative of general formula (I).

Diagram D

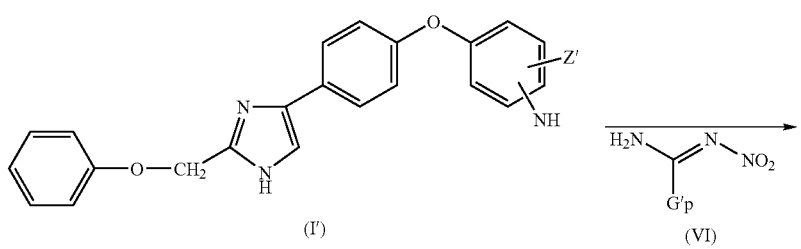

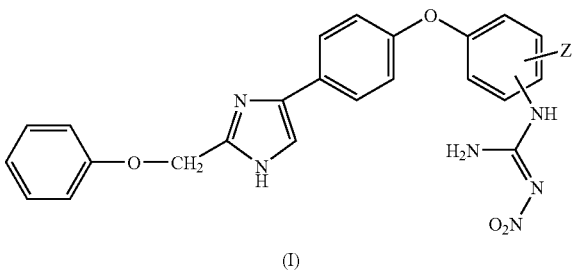

The derivatives of general formula (VI) can be obtained, for example, by firstly reacting in a polar solvent such as water, nitroguanidine and hydrazine hydrate then by condensing the product thus obtained with 2,4-pentadione in a polar solvent such as water for example.

As described in Diagram E below, the compounds of general formula (I) in which $R_1$ and $R_2$ are hydrogen atoms, X represents the —C(Y)— radical and Y the N—CN radical, can be obtained according to methods known to a person skilled in the art by condensing for example with the aniline compound of general formula (I') under reflux of a solvent such as dimethylformamide, the sodium salt of dicyanamide.

in which Z' has the meaning indicated above, is reacted with an isocyanate or isothiocyanate compound of formula (II) $R_1N=C=Y$ in which $R_1$ and Y have the meaning indicated above.

A subject of the invention is also a process for the preparation of a compound of formula (I) according to the invention and in which $R_1$ and $R_2$ are hydrogen atoms, X represents the —C(Y)— radical and Y an oxygen or sulfur atom, a process characterized in that (thio)phosgene of formula $Cl_2C=Y$ is reacted in an inert solvent with the compound of formula (I') as defined above, in order to form the iso(thio)cyanate derivative of general formula (III)

Diagram E

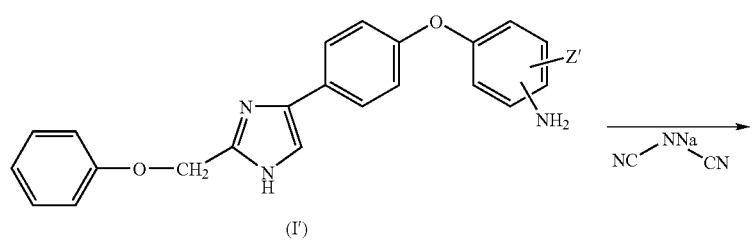

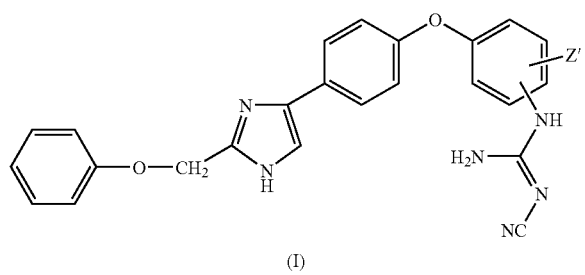

A subject of the invention is also a process for the preparation of a compound of formula (I) according to the invention and in which $R_2$ represents the hydrogen atom, $R_1$ represents the hydrogen atom, a $(C_1-C_6)$alkyl radical, an optionally substituted phenyl radical or an optionally substituted benzyl radical, X represents the —C(Y)— radical and Y an oxygen or sulfur atom, a process characterized in that a compound of formula (I')

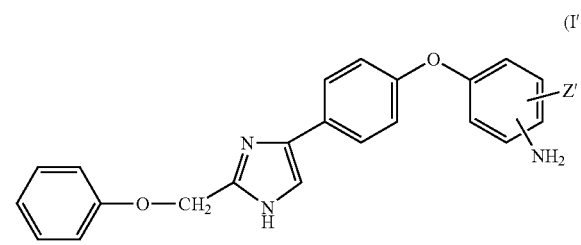

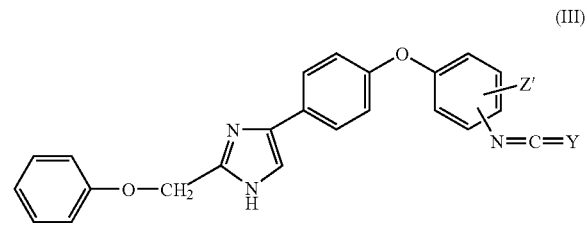

(III)

a stage followed by a condensation of gaseous ammonia in a solvent in order to form the compound of general formula (I).

A subject of the invention is also a process for the preparation of a compound of formula (I) according to the invention and in which $R_1$ represents the hydrogen atom, $R_2$ represents the hydrogen atom or an alkyl radical, and X represents an —$SO_2$— radical, a process characterized in that a compound of formula (I') as defined above, is reacted with a sulfonyl halide of formula $GpNR_2$—$SO_2$-Hal in which Gp is a protective group for the amine function and Hal represents a halo radical, in order to form compound (V)

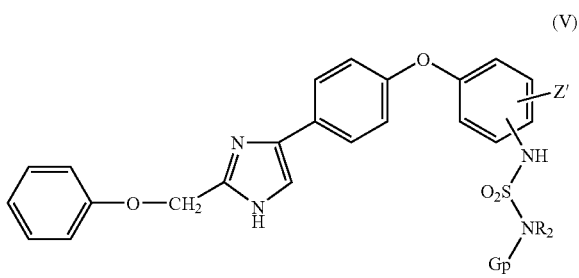

(V)

in which Z' is as defined in claim 1,
compound (V) thus formed which is deprotected in order to form compound (I).

A subject of the invention is also a process for the preparation of a compound of formula (I) according to the invention and in which $R_1$ and $R_2$ are hydrogen atoms and X represents a —C(Y)— radical and Y the N—$NO_2$ radical, a process characterized in that a to nitrated derivative of general formula (VI)

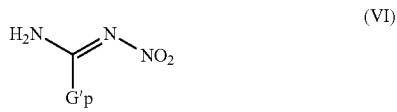

(VI)

in which G'p is a leaving group, is heated under reflux of a solvent, with the compound of general formula (I') as defined above.

A subject of the invention is also a process for the preparation of a compound of formula (I) according to the invention and in which $R_1$ and $R_2$ are hydrogen atoms and X represents a —C(Y)— radical and Y the N—CN radical, a process characterized in that the sodium salt of dicyanamide is condensed with a compound of formula (I') as defined above under reflux of a solvent.

The compounds of formula (I) according to the present invention have useful pharmacological properties. In this way it was discovered that the compounds of formula (I) of the present invention have an anti-tumoral (anti-cancerous) activity, and more particularly an inhibitory activity on tubulin polymerization. They can also have an anti-rheumatic activity. In addition, they can have an anti-inflammatory activity.

The compounds of the present invention can therefore be used in different therapeutic applications. They can advantageously be used for the treatment of cancer as defined previously and preferably cancers of the breast, colon, prostate, pancreas and melanomas. They can be also used for treating rheumatic or inflammatory diseases such as gout. An illustration of the pharmacological properties of the compounds of the invention will be found hereafter, in the experimental part.

A subject of the present Application is also pharmaceutical compositions containing, as active ingredient, at least one compound of formula (I) as defined above, as well as the addition salts with pharmaceutically acceptable mineral or organic acids of said compound of formula I, in combination with a pharmaceutically acceptable support.

By pharmaceutically acceptable salt is meant in particular the addition salts with inorganic acids such as hydrochloride, hydrobromide, hydroiodide, sulfate, phosphate, diphosphate and nitrate or with organic acids such as acetate, maleate, fumarate, tartrate, succinate, citrate, lactate, methanesulfonate, benzenesulfonate, p-toluenesulfonate, pamoate and stearate. Also included within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

A subject of the present Application is also the use of a compound of formula (I) according to the present invention, for the preparation of an anti-tumoral medicament.

A subject of the present Application is also the use of a compound of formula (I) according to the present invention, for the preparation of a medicament intended to inhibit tubulin polymerization.

A subject of the present Application is also the use of a compound of formula (I) according to the present invention, for the preparation of a medicament intended to treat rheumatic or inflammatory diseases.

A subject of the present Application is also the use of a compound of formula (I) according to the present invention, for the preparation of a medicament intended for treating gout.

The compounds of the present invention can be administered alone or simultaneously or sequentially in combination with other agents with anti-tumoral activity. Among the agents with anti-tumoral activity, there can be mentioned: the topoisomerase I inhibitors such as diflomotecan, irinotecan or topotecan; the topoisomerase II inhibitors; the inhibitors of tubulin polymerization such as navelbine; microtubule depolymerization inhibitors such as taxol; alkylating agents such as cyclophosphamide, the fosfamides or melphalan; the platinum derivatives such as cisplatin, carboplatin or oxaliplatin; antibiotics such as bleomycin or mitomycin; antimetabolites such as 5-fluorouracil; anti-hormonal agents and anti-growth factor agents.

The administration of a composition according to the invention can also be combined with radiotherapy.

The pharmaceutical composition can be in solid form, for example, powders, granules, tablets, gelatin capsules. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be for example water, organic solvents such as glycerol or glycols, as well as their mixtures, in varying proportions, in water, with added pharmaceutically acceptable oils or fats. The sterile liquid compositions can be used for intramuscular, intraperitoneal or sub-cutaneous injections and the sterile compositions can also be administered by intravenous route.

All the technical and scientific terms used in the present text have the meaning known to a person skilled in the art. Moreover, all the patents (or patent applications) as well as the other bibliographical references are incorporated by way of reference.

EXPERIMENTAL PART

According to the definitions of the variable Z and Z' groups, the compounds according to the invention can be prepared according to the different procedures A to E described above.

The following examples are given to illustrate the above procedures and should in no way be considered as limiting the scope of the invention.

Example 1

N-(4-methylphenyl)-N'-(4-{4-[2-(phenoxymethyl)-1H-imidazol-4-yl]phenoxy}phenyl)urea A mixture containing 4-{4-[2-(phenoxymethyl)-1H-imidazol-4-yl]phenoxy}aniline (0.2 g, 0.56 mmol) and paramethylphenylisocyanate (0.089 g, 0.67 mmol) in 3 ml of tetrahydrofuran is stirred for 24 hours at ambient temperature. The precipitate formed is filtered then the solid is stirred in a mixture of solvents such as isopropyl ether/ethyl acetate/isopropanol (5/4/1). After filtration then drying, a solid in the form of a beige powder is obtained with a yield of 73%.

NMR-$^1$H ($\delta$ ppm, DMSO): 2.24 (s, 3H); 5.07 (s, 2H); 6.94-7.94 (m, 18H); 8.51 (s, 1H); 8.60 (s, 1H); 12.4 (se, 1H)

MH+ experimental=491.20; M theoretical=491.56; Melting point: 192-194° C.

Example 2

N-butyl-N'-(4-{4-[2-(phenoxymethyl)-1H-imidazol-4-yl]phenoxy}phenyl)urea trifluoroacetate A mixture containing 4-{4-[2-(phenoxymethyl)-1H-imidazol-4-yl]phenoxy}aniline (0.2 g, 0.56 mmol) and butylisocyanate (0.094 g, 0.84 mmol) in 3 ml of tetrahydrofuran is stirred for a day at ambient temperature. Aminomethylpolystyrene resin EHL (Novabiochem, 200-400 mesh, 2% DVB) (200 mg, approximately 1 mmol) is added and stirring is maintained for three hours. After filtration on frit then concentration of the filtrate in a rotavapor, the residue obtained is passed through an RP18 silica column (eluent: acetonitrile-trifluoroacetic acid 0.1N: 5-5); a beige-coloured powder is obtained with a yield of 43%.

NMR-$^1$H ($\delta$ ppm, DMSO): 0.83-0.91 (m, 5H); 1.39-1.43 (m, 2H); 3.07-3.08 (m, 2H); 5.3 (s, 2H); 6.11 (m, 1H); 6.96-7.44 (m, 13H); 7.91 (m, 1H); 8.44 (m, 1H)

MH+ experimental=457.30; M theoretical=456.54; Melting point: 85-87° C.

Example 3

N-(4-{4-[2-(phenoxymethyl)-1H-imidazol-4-yl]phenoxy}phenyl)urea

A mixture containing 4-{4-[2-(phenoxymethyl)-1H-imidazol-4-yl]phenoxy}aniline (0.2 g, 0.56 mmol) and trimethylsilyl-isocyanate (0.11 ml, 0.84 mmol) in 3 ml of tetrahydrofuran is stirred for 24 hours at ambient temperature. Aminomethylpolystyrene resin EHL (Novabiochem, 200-400 mesh, 2% DVB) (200 mg, approximately 1 mmol) is added and stirring is maintained for three hours. After filtration on frit, the filtrate is concentrated in a rotavapor. Isopropyl acetate and traces of isopropanol are added to the residue obtained. The mixture is heated to dissolution followed by filtration on frit then left to crystallize for 24 hours. After filtration then drying under a bell jar, a light beige-coloured powder is obtained.

NMR-$^1$H ($\delta$ ppm, DMSO): 5.06 (s, 2H); 5.79 (s, 2H); 6.90-7.74 (m, 14H); 8.50 (s, 1H); 12.35 (se, 1H)

MH+ experimental=401.20; M theoretical=400.44; Melting point: 200-202° C.

Example 4

N-ethyl-N'-(4-{4-[2-(phenoxymethyl)-1H-imidazol-4-yl]phenoxy}phenyl)thiourea

A mixture containing 4-{4-[2-(phenoxymethyl)-1H-imidazol-4-yl]phenoxy}aniline (0.5 g, 1.40 mmol) and ethylisothiocyanate (0.162 g, 1.70 mmol) in 10 ml of ethanol is heated for four hours under reflux. 5 ml of dichloromethane and traces of ethyl acetate and ethanol are added to the residue obtained. The medium is stirred for thirty minutes, then filtered and the solid obtained is dried. A cream-coloured powder is obtained with a yield of 45%.

NMR-$^1$H ($\delta$ ppm, DMSO): 1.1 (m, 3H); 3.4 (m, 2H); 5.07 (s, 2H); 6.94-7.78 (m, 15H); 9.35 (se, 1H); 12.40 (se, 1H)

MH+ experimental=445.20; M theoretical=444.570; Melting point: 178-180° C.

Example 5

N-ethyl-N'-(2-fluoro-4-{4-[2-(phenoxymethyl)-1H-imidazol-4-yl]phenoxy}phenyl)thiourea A mixture containing 2-fluoro-4-{4-[2-(phenoxymethyl)-1H-imidazol-4-yl]phenoxy}aniline (1 g, 2.66 mmol) and ethylisothiocyanate (0.31 g, 2.32 mmol) in 20 ml of ethanol is heated for five hours under reflux. The reaction mixture is concentrated in a rotavapor. After passing the residue obtained through a silica column (eluent: dichloromethane/ethanol/liquid ammonia 96/2/2), a yellow-coloured powder is obtained with a yield of 11%.

NMR-$^1$H ($\delta$ ppm, DMSO): 1.06 (t, 3H); 3.46 (me, 2H); 5.08 (s, 2H); 6.73-7.82 (m, 15H); 9.03 (se, 1H)

MH+ experimental=463.20; M theoretical=462.55; Melting point: 105-107° C.

Example 6

N-(2-fluoro-4-{4-[2-(phenoxymethyl)-1H-imidazol-4-yl]phenoxy}phenyl)thiourea 1) 4-[4-(3-fluoro-4-isothiocyanatophenoxy)phenyl]-2-(phenoxymethyl)-1H-imidazole At 23° C. and under an argon atmosphere, triethylamine (3.34 g; 0.024 mol) is added to a solution containing 2-fluoro-4-{4-[2-(phenoxymethyl)-1H-imidazol-4-yl]phenoxy}aniline (3 g, 0.008 mol) in tetrahydrofuran (120 ml). The reaction medium is cooled down to 0° C. then the thiophosgene compound (1.01 g; 0.0088 mol) is added dropwise. Stirring is maintained at this temperature for thirty minutes then the reaction medium is returned to 23° C. and stirred at this temperature for twenty minutes. 60 ml of water and 150 ml of ethyl ether are added to the reaction medium. The two phases are separated then the organic phase is washed with a saturated sodium chloride solution. The organic phase is dried over sodium sulfate, followed by concentration to dryness then the product obtained is triturated in isopentane with traces of dichloromethane. The solid obtained is filtered then dried. A yellow-coloured powder is obtained with a yield of 78%.

MH+ experimental=418.20; M theoretical=417.462

2) N-(2-fluoro-4-{4-[2-(phenoxymethyl)-1H-imidazol-4-yl]phenoxy}phenyl)thiourea

The 4-[4-(3-fluoro-4-isothiocyanatophenoxy)phenyl]-2-(phenoxymethyl)-1H-imidazole compound obtained previously (2.58 g, 0.0062 mol) is solubilized at 23° C. in 50 ml of a mixture of solvents dichloromethane/methanol/tetrahydrofuran 6/3/1. The reaction medium is cooled down to 0° C. then gaseous ammonia is bubbled through to saturation. Stirring is maintained for thirty minutes at this temperature then after the reaction medium is returned to ambient temperature, stirring is continued for another thirty minutes. The reaction medium is evaporated in a rotavapor then the solid obtained is triturated in a mixture of isopropyl ether and isopropyl alcohol (5:5). The solid obtained is filtered then recrystallized from a minimum amount of isopropyl alcohol whilst warm. The reaction medium is left to cool down then filtered. A light brown-coloured powder is obtained with a yield of 42%.

NMR-$^1$H ($\delta$ ppm, DMSO): 5.08 (s, 2H); 6.79-7.82 (m, 15H); 9.26 (s, 1H); 12.4 (se, 1H)

MH+ experimental=435.20; M theoretical=434.493; Melting point: 171-173° C.

Example 7

N-isopropyl-N'-(4-{4-[2-(phenoxymethyl)-1H-imidazol-4-yl]phenoxy}phenyl)urea

A mixture containing 4-{4-[2-(phenoxymethyl)-1H-imidazol-4-yl]phenoxy}aniline (0.2 g, 0.56 mmol) and isopropylisocyanate (0.155 g, 1.8 mmol) in 3 ml of dimethylformamide is heated at 100° C. for two hours then stirred at ambient temperature for two hours. 20 ml of water and 30 ml of ethyl acetate are added, followed by extraction, then the organic phase is washed with a saturated sodium chloride solution. The organic phase is dried over sodium sulfate. After evaporation to dryness, the oil obtained is triturated in isopentane. After filtration then drying, the solid obtained is purified on a silica column (eluent dichloromethane-ethanol-ammonia 96/2/2) and a pink-cream coloured powder is obtained with a yield of 20%.

NMR-$^1$H ($\delta$ ppm, DMSO): 1.07 (d, 6H); 3.74 (m, 1H); 5.06 (s, 2H); 5.93 (m, 1H); 6.91-7.74 (m, 14H); 10.19 (s, 1H); 12.4 (se, 1H)

MH+ experimental=443.20; M theoretical=442.516; Melting point: 184-186° C.

Example 8

N-(4-{4-[2-(phenoxymethyl)-1H-imidazol-4-yl]phenoxy}phenyl)-N'-phenylurea

A mixture containing 4-{4-[2-(phenoxymethyl)-1H-imidazol-4-yl]phenoxy}aniline (0.2 g, 0.56 mmol) and phenylisocyanate (0.136 g, 1.12 mmol) in 3 ml of dimethylformamide is heated at 100° C. for two hours. After returning to ambient temperature 20 ml of water and 30 ml of ethyl acetate are added followed by extraction, then the organic phase is washed with a saturated sodium chloride solution. The organic phase is dried over sodium sulfate, filtered and concentrated to dryness under vacuum. The solid obtained is purified on a silica column (eluent: dichloromethane-ethanol-ammonia 96-2-2) in order to obtain a white-coloured powder with a yield of 21%.

NMR-$^1$H ($\delta$ ppm, DMSO): 5.08 (s, 2H); 6.94-7.77 (m, 19H); 8.52 (m, 2H); 12.4 (se, 1H).

MH+ experimental=477.20; M theoretical=476.534; Melting point: 146-148° C.

Example 9

N-(4-methylbenzyl)-N'-(4-{4-[2-(phenoxymethyl)-1H-imidazol-4-yl]phenoxy}phenyl)urea A mixture containing 4-{4-[2-(phenoxymethyl)-1H-imidazol-4-yl]phenoxy}aniline (0.2 g, 0.56 mmol) and 4-methylbenzylisocyanate (0.17 g, 1.12 mmol) in 3 ml of dimethylformamide is heated at 100° C. for two hours. After returning to ambient temperature 20 ml of water and 30 ml of ethyl acetate are added, followed by extraction then the organic phase is washed with a saturated sodium chloride solution. The organic phase is dried over sodium sulfate, filtered and concentrated to dryness under vacuum. The solid obtained is stirred in 5 ml of a mixture of solvents such as ethyl ether/ethyl acetate/isopropanol 6/3/1. The solid obtained is filtered then dried. A cream-coloured powder is obtained with a yield of 21%.

NMR-$^1$H ($\delta$ ppm, DMSO): 4.16-4.25 (m, 2H); 5.07 (s, 2H); 6.31-6.52 (m, 1H); 6.91-7.75 (m, 20H); 8.52 (m, 1H); 10.18 (s, 1H) 12.4 (se, 1H)

MH+ experimental=477.20; M theoretical=476.534; Melting point: 146-148° C.

Example 10

N-ethyl-N'-(4-{4-[2-(phenoxymethyl)-1H-imidazol-4-yl]phenoxy}phenyl)urea trifluoroacetate A mixture containing 4-{4-[2-(phenoxymethyl)-1H-imidazol-4-yl]phenoxy}aniline (0.2 g, 0.56 mmol) and ethylisocyanate (0.066 ml, 0.84 mmol) in 3 ml of tetrahydrofuran is stirred for a day at ambient temperature. Aminomethylpolystyrene resin EHL (Novabiochem, 200-400 mesh, 2% DVB) (200 mg, approximately 1 mmol) is added and stirred for three hours, followed by filtration on frit then the filtrate is concentrated in a rotavapor. After passing the residue obtained through an RP18 silica column (eluent acetonitrile/trifluoroacetic acid 0.1N 5:5), a solid is obtained in the form of brown gum with a yield of 16%.

NMR-$^1$H ($\delta$ ppm, DMSO): 0.96-1.03 (m, 3H); 3.2-4.2 (me, 1H); 3.60 (m, 2H); 5.29 (s, 2H); 6.11 (se, 1H); 6.95-7.89 (m, 14H); 8.48 (s, 1H); 12-15 (se, 1H)

MH+ experimental=429.20; M theoretical=428.90

Example 11

N-(2-fluoro-4-{4-[2-(phenoxymethyl)-1H-imidazol-4-yl]phenoxy}phenyl)sulfamide hydrochloride 1) tert-butyl {[(2-fluoro-4-{4-[2-(phenoxymethyl)-1H-imidazol-4-yl]phenoxy}phenyl)amino]sulfonyl}carbamate At 0° C., the compound 2-fluoro-4-{4-[2-(phenoxymethyl)-1H-imidazol-4-yl]phenoxy}aniline (1.5 g, 4 mmol)

and triethylamine (0.63 ml, 4.52 mmol) are solubilized in 10 ml of dichloromethane. A mixture containing sulfonyl isocyanate chloride (0.623 g, 4.40 mmol) and tert-butanol (0.325 g, 4.40 mmol) in 10 ml of dichloromethane is added to this solution at 0° C. The reaction medium is returned to ambient temperature then stirred for two hours. After evaporation of the solvent, the solid obtained is purified on a silica column (eluent: dichloromethane-methanol: 95-5). After washing in dichloromethane then filtration, a yellow-coloured powder is obtained with a yield of 75%.

2) N-(2-fluoro-4-{4-[2-(phenoxymethyl)-1H-imidazol-4-yl]phenoxy}phenyl)sulfamide hydrochloride At ambient temperature, gaseous hydrochloric acid is bubbled through a mixture containing tert-butyl{[(2-fluoro-4-{4-[2-(phenoxymethyl)-1H-imidazol-4-yl]phenoxy}phenyl)amino]sulfonyl}carbamate (1.66 g, 2.9 mmol) isolated previously from a mixture of solvents such as ethyl acetate/ethanol (3/1) to saturation. The precipitate is filtered then washed with isopropyl ether and isopropanol. After drying, a solid in the form of a white powder is obtained with a yield of 80%.

NMR-$^1$H (δ ppm, DMSO): 5.43 (s, 2H); 6.87-8.09 (m, 15H); 9.01 (s, 1H); 12.4 (se, 2H)

MH+ experimental=455.10; M theoretical=454.48; Melting point: 185-187° C.

Example 12

N"-cyano-N-(2-fluoro-4-{4-[2-(phenoxymethyl)-1H-imidazol-4-yl]phenoxy}phenyl)guanidine In a sealed glass tube suitable for microwave heating, the compound 2-fluoro-4-{4-[2-(phenoxymethyl)-1H-imidazol-4-yl]phenoxy}aniline (0.1 g, 0.27 mmol) and sodium dicyanamide (37 mg, 0.4 mmol) in 2.5 ml of dimethylformamide and 0.5 ml of hydrochloric acid 1N are heated at 75° C. in a microwave oven (Biotage, Emrys Optimiser) for 900 seconds. The reaction medium is evaporated to dryness. After passing the residue obtained through a silica column (eluent dichloromethane/ethanol 93/7), a solid in the form of white powder is obtained with a yield of 31%.

NMR-$^1$H (δ ppm, DMSO): 5.07 (s, 2H); 6.82-7.81 (m, 15H); 8.72 (s, 1H); 12.40 (se, 1H)

MH+ experimental=443.20; M theoretical=442.452; Melting point: 139-141° C.

Example 13

N-(2-fluoro-4-{4-[2-(phenoxymethyl)-1H-imidazol-4-yl]phenoxy}phenyl)-N"-nitroguanidine 1) N'-nitrohydrazinecarboximidamide The hydrazine hydrate compound (1.05 ml, 21.6 mmol) is added dropwise to a solution heated to 55° C. containing the nitroguanidine compound (2 g, 19.2 mmol) in 25 ml of water. Stirring is maintained for fifteen minutes until a clear orange-yellow reaction medium is obtained. After cooling down, 2 ml of 37% hydrochloric acid is added. The reaction medium is filtered then the solid obtained is washed with iced water. The solid is then recrystallized from a minimum amount of water in order to produce after filtration a white powder with a yield of 35%. Melting point: 187-189° C.

2) 3,5-dimethyl-N'-nitro-1H-pyrazole-1-carboximidamide 2.7 ml of acetic acid and 2,4-pentadione (0.785 mg, 7.83 mmol) are added to a mixture heated under reflux containing the N'-nitrohydrazinecarboximidamide compound isolated previously (0.5 g, 4.20 mmol) in 15 ml of water. The reaction medium is returned to ambient temperature then filtered. The solid obtained is washed with dichloromethane. A white solid in the form of white powder is obtained with a yield of 89%.

MH+ experimental=184.10; M theoretical=183.17

3) N-(2-fluoro-4-{4-[2-(phenoxymethyl)-1H-imidazol-4-yl]phenoxy}phenyl)-N"-nitroguanidine In a sealed glass tube suitable for microwave heating, 2-fluoro-4-{4-[2-(phenoxymethyl)-1H-imidazol-4-yl]phenoxy}aniline (0.6 g, 1.6 mmol) and 3,5-dimethyl-N'-nitro-1H-pyrazole-1-carboximidamide (0.296 g, 1.6 mmol) in 5 ml of methanol are heated at 150° C. in a microwave oven (Biotage, Emrys Optimiser) for 2700 seconds. The reaction medium is evaporated to dryness. After passing the residue obtained through a silica column (eluent dichloromethane/ethanol 98/2), a solid is obtained in the form of white powder.

NMR-$^1$H (δ ppm, DMSO): 5.08 (s, 2H); 6.86-7.83 (m, 13H); 8.2-9.5 (m, 3H); 12.40 (se, 1H)

MH+ experimental=463.20; M theoretical=462.439; Melting point: 193-195° C.

Pharmacological Study

The anti-proliferative activity of the compounds of the present invention is determined by applying the following experimental procedure:

The different cell lines are incubated at 37° C. in an atmosphere containing 5% $CO_2$ (Format Scientific incubators) in DMEM (Dulbecco's modified Eagle's medium) at 4.5 g/l of glucose to which 10% calf serum inactivated by heat, 50 U/ml of penicillin, 50 µg/ml of streptomycin and 2 mM of glutamine (Gibco) have been added.

The inhibition of the cell proliferation is measured by the WST colorimetric test (tetrazolium salt, Boehringer Mannheim, Meylan, France). The cells are seeded in 96-well microplates (TPP) at a rate of 1300 cells per well in the case of DU145, and 1200 in the case of MIA-Pa-Ca-2 in 95 µl of culture medium. 24 hours after the seeding, 5 µl of drugs are added at different concentrations (the product is dissolved in DMA at 10-3M then it is diluted in culture medium). The final concentrations range from 500 nM to 0.97 nM. After incubation for 72 hour, 10 µl of WST per well is added and determination of the absorbance is carried out at 450 nm 2 hours later (Victor, Perkin Elmer).

Each experiment is carried out twice and is the result of the measurement of the absorbance of eight wells. For each product, the $IC_{50}$ measurement corresponding to the concentration of the product which leads to 50% cell growth inhibition, is determined by a linear regression calculation (linear deviation, linearity deviation and difference between the experiments, TSAR calculation program) on the linear part of the sigmoid.

The $IC_{50}$ values obtained are of the order of 20 nM or less, and for certain compounds they vary from 1 nM to 10 nM.

The invention claimed is:
1. A compound of formula (I)

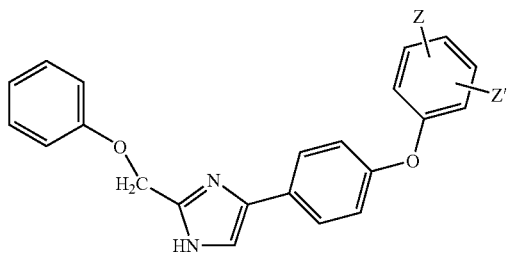

(I)

in which:

Z' represents a hydrogen atom or a halo radical;
Z represents a radical of formula —NH—SO$_2$—NR$_1$R$_2$;
R$_1$ and R$_2$ represent, independently, a hydrogen atom, a (C$_1$-C$_6$)alkyl radical, phenyl optionally substituted by a (C$_1$-C$_6$)alkyl radical, or benzyl optionally substituted on the ring by a (C$_1$-C$_6$)alkyl radical; or
a pharmaceutically acceptable salt of said compound.

2. The compound according to claim 1, wherein R$_1$ and R$_2$ represent, independently, a hydrogen atom or a (C$_1$-C$_6$)alkyl radical.

3. The compound according to claim 1 wherein R$_1$ represents a hydrogen atom and R$_2$ represents a hydrogen atom or a (C$_1$-C$_6$)alkyl radical.

4. The compound according to claim 1 wherein Z is in para position.

5. The compound according to claim 1 wherein Z' is in meta position.

6. The compound according to claim 5, wherein Z' represents a halo radical.

7. The compound according to claim 1 wherein said compound is:
N-(2-fluoro-4-{4-[2-(phenoxymethyl)-1H-imidazol-4-yl]phenoxy}phenyl)sulfamide hydrochloride; or
a pharmaceutically acceptable salt of said compound.

8. A process for the preparation of a compound of formula (I) according to claim 1 in which R$_1$ represents a hydrogen atom, R$_2$ represents a hydrogen atom or an alkyl radical, and X represents an —SO$_2$— radical, said process comprising the steps of:

(a) reacting a compound of formula (I')

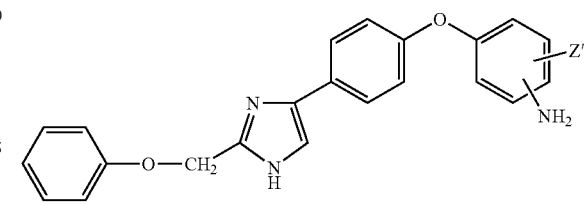

(I')

in which Z' is a hydrogen atom or a halo radical
with a sulfonyl halide of formula GpNR$_2$—SO$_2$-Hal wherein Gp is a protecting group for the amine function and Hal represents a halo radical, thereby forming a compound of formula (V)

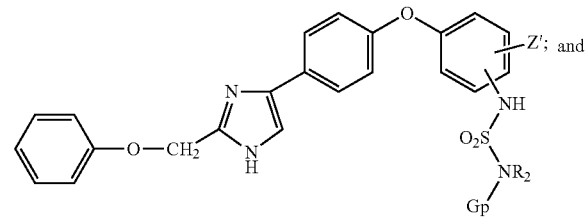

(V)

(b) deprotecting said compound (V) to form compound (I).

9. A pharmaceutical composition comprising a compound according to claim 1 as active ingredient, in combination with a pharmaceutically acceptable support.

* * * * *